United States Patent [19]

Kay et al.

[11] Patent Number: 4,709,038

[45] Date of Patent: Nov. 24, 1987

[54] BIOLOGICALLY ACTIVE AMIDES

[75] Inventors: Ian T. Kay, Wokingham; Robert A. Noon, Maidenhead, both of England

[73] Assignee: Imperial Chemical Industries PLC, London, England

[21] Appl. No.: 696,719

[22] Filed: Jan. 31, 1985

Related U.S. Application Data

[62] Division of Ser. No. 408,894, Aug. 17, 1982, Pat. No. 4,515,959.

[30] Foreign Application Priority Data

Sep. 30, 1981 [GB] United Kingdom ................. 8129521

[51] Int. Cl.$^4$ ................. C07D 213/55; C07D 213/56; C07D 333/38; C07D 307/66
[52] U.S. Cl. .................................... 546/316; 546/323; 549/72; 549/366; 549/436; 549/487; 560/41; 564/158
[58] Field of Search ....................... 546/316, 323, 366; 549/72, 487, 436; 564/158; 560/41

[56] References Cited

U.S. PATENT DOCUMENTS 3,228,833 1/1966 Crounse et al. .
3,415,838 12/1968 Crounse et al. .
4,131,735 12/1978 van Poucke .
4,515,959 5/1985 Kay .................................... 564/158

FOREIGN PATENT DOCUMENTS 827777 10/1975 Belgium .
830211 12/1975 Belgium .
852808 9/1977 Belgium .
776711 1/1968 Canada .
0059536 9/1982 European Pat. Off. ............ 546/316
0061836 10/1982 European Pat. Off. ............ 549/72
2140438 2/1973 Fed. Rep. of Germany .
2828265 1/1980 Fed. Rep. of Germany .
7204894 10/1972 Netherlands .
2052499A 1/1981 United Kingdom .

OTHER PUBLICATIONS

"Zhur. Obshch. Khim., vol. 38, No. 11, pp. 2353-2358 (1968).
Tetrahedron, vol. 33, No. 8, 1977, pp. 881-883, Pergamon Press, GB; Z. Bernstein et al.: "Synthesis of N-Substituted Azirdine-2-Carboxylates.
Chem. Abs., vol. 79, No. 1, Jul. 9, 1973, p. 448, Abs. No. 5280g, Columbus, Ohio, D. Mathies: "Amino Alkylation by a Transfer Reaction".
Synthesis, "International Journal of Methods in Synthetic Organic Chemistry", No. 7, Jul. 1972, Academic Press, N.Y./London, D. Matthies, Uber die Amidoalkylierung von Azolen:, p. 380.
Chem. Abs. 69(23): 99601v (1968).

Primary Examiner—Robert T. Bond
Attorney, Agent, or Firm—Cushman, Darby & Cushman

[57] ABSTRACT

Herbicidal and fungicidal compounds of the formula

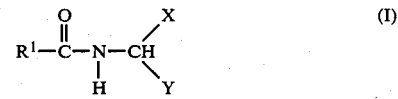

wherein $R^1$ is (a) a phenyl group optionally substituted by one or more halogen atoms, cyano groups, alkoxy groups, methylene- or ethylene-dioxy groups, alkyl groups, or haloalkyl groups (e.g. trifluoromethyl groups); or (b) a heteroaromatic group optionally substituted by one or more alkyl groups, haloalkyl groups or halogen atoms X is a 5-membered heteroaromatic radical linked by a ring nitrogen atom to the carbon atom bearing Y, and optionally substituted by one or more alkyl groups, and Y is a CN group; a —CSNH$_2$ group; a —CO$_2$R$^4$ group wherein R$^4$ is an esterifying radical, for example an alkyl radical; or an amide group —CONR$^5$R$^6$ wherein each of R$^5$ and R$^6$ may be a hydrogen atom or an alkyl radical (e.g. an alkyl radical of 1 to 6 carbon atoms).

2 Claims, No Drawings

BIOLOGICALLY ACTIVE AMIDES

This is a division of application Ser. No. 408,894, filed Aug. 17, 1982 now U.S. Pat. No. 4,515,959.

This invention relates to amide compounds useful as herbicides and fungicides, and to herbicidal and fungicidal compositions and processes utilising them.

According to the present invention there are provided amide compounds of the formula (I)

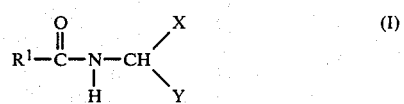

wherein $R^1$ is (a) a phenyl group optionally substituted by one or more halogen atoms, cyano groups, alkoxy groups, methylene- or ethylene-dioxy groups, alkyl groups, or haloalkyl groups (eg. trifluoromethyl groups); or (b) a heteroaromatic group optionally substituted by one or more alkyl groups, haloalkyl groups or halogen atoms X is a 5-membered heteroaromatic radical linked by a ring nitrogen atom to the carbon atom bearing Y, and optionally substituted by one or more alkyl groups, and Y is a CN group; a —$CSNH_2$ group; a —$CO_2R^4$ group wherein $R^4$ is an esterifying radical, for example an alkyl radical; or an amide group —$CONR^5R^6$ wherein each of $R^5$ and $R^6$ may be a hydrogen atom or an alkyl radical (eg. an alkyl radical of 1 to 6 carbon atoms).

In the foregoing definition, the term halogen is intended to include fluorine, chlorine, bromine and iodine. The terms alkyl, alkoxy, and haloalkyl refer to radicals containing for example from one to six or more carbon atoms. Particular examples of these radicals include methyl, ethyl, propyl, isopropyl, methoxy, ethoxy, and trifluoromethyl. The term heteroaromatic radical includes, for example the furyl, thiophenyl, and pyridyl radicals. The term 5-membered heteroaromatic radical includes for example, the 1-pyrazolyl, 1-tetrazolyl and 1-(1,2,4-triazolyl) radicals, and such radicals substituted by one or more lower alkyl (eg. methyl) radical.

One sub-group of compounds according to the invention comprises compounds wherein Y is a cyano group, and $R^1$ and X are as hereinbefore defined. Within this sub-group, a further group is formed by compounds wherein $R^1$ is an optionally substituted phenyl radical, and X is a 1-pyrazolyl, 1-tetrazolyl, or 1-(1,2,4-triazolyl) radical. In this group, the phenyl group $R^1$ may be, for example substituted in either the 3 or the 5 position, or in both the 3,4 and the 5 position, or, preferably in both the 3 and the 4-position by, for example, methyl or chlorine. Compounds in which the phenyl group $R^1$ bears a 4-substituted alone, or a 3 and a 4 position substituent, eg. $CH_3$, Cl, Br, F, $CH_3O$, or a 3,4-methylenedioxy or ethylene-dioxy substituent are of particular interest as fungicides.

In a further aspect the invention provides amide compounds as defined above wherein $R^1$ is phenyl optionally substituted at the 3-, 4- or 5-positios with one or more halogens, or alkyl, alkoxy, trifluoromethyl, or alkylenedioxy groups; X is 1-pyrazolyl, 1-(1,2,4-triazolyl); 1-tetrazolyl; 3- or 5-methyl-1-pyrazolyl, or 3,5-dimethylpyrazolyl; and Y is CN, $CONH_2$, or $CO_2CH_3$ as defined above. In a still further aspect, the invention provides amide compounds wherein $R^1$ is phenyl substituted at the either 3- or 4-position, or both, with chlorine, fluorine, bromine, methyl, methoxy or methylenedioxy (3,4-only); X is 1-pyrazolyl; and Y is CN.

Particular examples of compounds according to the invention are listed in Table 1 below together with their melting points and a reference to the method by which they were prepared. The methods of preparation are described below.

TABLE 1

| COMPOUND NUMBER | $R^1$ | $R^2$ | $R^3$ | X | Y | MELTING POINT °C. | METHOD |
|---|---|---|---|---|---|---|---|
| 1 | 3-Cl.C6H4 | | | 1-(1,2,4-triazolyl) | CN | 157–159 | A |
| 2 | 3,5-Cl2.C6H3 | | | 1-(1,2,4-triazolyl) | CN | 185 | A |
| 3 | 3-Cl.C6H4 | | | 1-pyrazolyl | CN | 149–150 | A |
| 4 | 3-F.C6H4 | | | 1-pyrazolyl | CONH2 | 181–183 | A |
| 5 | 3-F.C6H4 | | | 1-pyrazolyl | CN . | 155–158 | A |
| 6 | 3-Cl.C6H4 | | | 1-(1,2,4-triazolyl) | CONH2 | 206–208 | A |
| 7 | 3,5-Cl2.C6H3 | | | 1-(1,2,4-triazolyl) | CONH2 | — | A |
| 8 | 3-Br.C6H4 | | | 1-(1,2,4-triazolyl) | CONH2 | 199–201 | A |
| 9 | 3-Br.C6H4 | | | 1-pyrazolyl | CONH2 | 185–187 | A |
| 10 | 3,5-(CH3)2C6H4 | | | 1-pyrazolyl | CO2CH3 | 163–165 | A |
| 11 | 3-Br.C6H4 | | | 1-pyrazolyl | CN | 144–147 | A |
| 12 | 3-Br.C6H4 | | | 1-(1,2,4-triazolyl) | CN | 163–164 | A |
| 13 | 3,5-(CH3)2.C6H4 | | | 1-pyrazolyl | CONH2 | 193–195 | B |
| 14 | 3,5-(CH3)2.C6H4 | | | 1-pyrazolyl | CN | 180–183 | B |
| 15 | 3-CF3.C6H4 | | | 1-pyrazolyl | CONH2 | 178–180 | A |
| 16 | 3-CF3.C6H4 | | | 1-(1,2,4-triazolyl) | CONH2 | 190–192 | A |
| 17 | 3,5-Cl2.C6H4 | | | 1-pyrazolyl | CONH2 | 202–205 | A |
| 18 | 3-CF3.C6H4 | | | 1-pyrazolyl | CN | 145–148 | A |
| 19 | 3-CF3C6H4 | | | 1-(1,2,4-triazolyl) | CN | 160–162 | A |
| 20 | 3,5-Cl2.C6H3 | | | 1-pyrazolyl | CN | 173–175 | A |
| 21 | 3-CH3.C6H4 | | | 1-pyrazolyl | CO2CH3 | 98–100 | B |
| 22 | 3-CH3.C6H4 | | | 1-pyrazolyl | CONH2 | 151–152 | B |
| 23 | 2-furyl | | | 1-pyrazolyl | CO2CH3 | 127–128 | B |
| 24 | 3-CH3.C6H4 | | | 1-pyrazolyl | CN | 137–139 | B |
| 25 | 2-furyl | | | 1-pyrazolyl | CONH2 | 161–163 | B |
| 26 | 2-furyl | | | 1-pyrazolyl | CN | 134–135 | B |
| 27 | 3,4-Cl2C6H3 | | | 1-pyrazolyl | CONH2 | 187–189 | A |
| 28 | 3,4-Cl2.C6H3 | | | 1-pyrazolyl | CN | 174–176 | A |
| 29 | 5-bromo-2-furyl | | | 1-pyrazolyl | CO2CH3 | 120–121 | B |
| 30 | 3,5-Cl2.C6H3 | | | 3-methyl-1-pyrazolyl and 3-methyl-2-pyrazolyl | CONH2 | — | A |
| 31 | 3-I.C6H4 | | | 1-pyrazolyl | CONH2 | Decomp | A |

TABLE 1-continued

| COMPOUND NUMBER | R¹ | R² | R³ | X | Y | MELTING POINT °C. | METHOD |
|---|---|---|---|---|---|---|---|
| 32 | 3-CH₃O.C₆H₄ | | | 1-pyrazolyl | CO₂CH₃ | 102-104 | B |
| 33 | 3-CH₃O.C₆H₄ | H | H | 1-pyrazolyl | CONH₂ | 159-162 | B |
| 34 | C₆H₅ | H | H | 1-pyrazolyl | CONH₂ | 183-186 | A |
| 35 | C₆H₅ | H | H | 1-pyrazolyl | CN | 169-174 | A |
| 36 | 3-CH₃O.C₆H₄ | H | H | 1-pyrazolyl | CN | 128-130 | B |
| 37 | 3-I.C₆H₄ | H | H | 1-pyrazolyl | CN | 172-175 | A |
| 38 | 3,5-Cl₂.C₆H₃ | H | H | 3-methyl-1-pyrazolyl | CN | 169-171 | A |
| 39 | 4-F.C₆H₄ | H | H | 1-pyrazolyl | CONH₂ | 161-162 | A |
| 40 | 4-F.C₆H₄ | H | H | 1-pyrazolyl | CN | 123-124 | A |
| 41 | 3,4-(CH₃)₂.C₆H₃ | H | H | 1-pyrazolyl | CONH₂ | 163-164 | A |
| 42 | 3,4-(CH₃)₂.C₆H₃ | H | H | 1-pyrazolyl | CN | 162-163 | A |
| 43 | 2-bromo-5-furyl | H | H | 1-pyrazolyl | CN | 156-158 | B |
| 44 | 3,5-(CH₃)₂.C₆H₃ | H | H | 3,5-(CH₃)₂—1-pyrazolyl | CN | 235-237 | A |
| 45 | 3,5-(CH₃)₂.C₆H₃ | H | H | 1-(1,2,4-triazolyl) | CONH₂ | 190-193 | A |
| 46 | 3,5-(CH₃)₂.C₆H₃ | H | H | 1-(1,2,4-triazolyl) | CN | 170-172 | A |
| 47 | (CH₃)₂CHCH₂CH₂ | H | H | 1-pyrazolyl | CO₂CH₃ | 104-106 | B |
| 48 | 3-F.C₆H₄ | H | H | 1-tetrazolyl | CN | 120 | A |
| 49 | 3,5-Cl₂.C₆H₃ | H | H | 1-pyrazolyl | CO₂CH₃ | 182-184 | B |
| 50 | 3-F.C₆H₄ | H | H | 1-tetrazolyl | CONH₂ | 171-173 | A |
| 51 | (CH₃)₂CH—CH=CH— | | | 1-pyrazolyl | CN | Oil | B |
| 52 | 2-CH₃—5-thienyl | | | 1-pyrazolyl | CO₂CH₃ | 146-147 | B |
| 53 | 3,5-Br₂.C₆H₃ | | | 1-pyrazolyl | CONH₂ | 210-215 | A |
| 54 | 2-CH₃—5-thienyl | | | 1-pyrazolyl | CN | 130-131 | B |
| 55 | 3,5-Cl₂.C₆H₃ | | | 3,5-(CH₃)₂—1-pyrazolyl | CONH₂ | 219-220 | A |
| 56 | 3,5-Cl₂.C₆H₃ | | | 3,5-(CH₃)₂—1-pyrazolyl | CN | 212-214 | A |
| 57 | C₆H₅ | | | 3-CH₃—1-pyrazolyl | CONH₂ | 207-211 | A |
| 58 | C₆H₅ | | | 3-CH₃—1-pyrazolyl | CN | 136-137 | A |
| 59 | 3,5-Cl₂.C₆H₃ | | | 3-CH₃—1-pyrazolyl | CN | 169-171 | A |
| 60 | 3,5-F₂.C₆H₃ | | | 1-pyrazolyl | CONH₂ | 192-193 | A |
| 61 | 3,5-F₂.C₆H₃ | | | 1-pyrazolyl | CN | 166-168 | A |
| 62 | 3,5-Cl.C₆H₃ | | | 1-pyrazolyl | CSNH₂ | 172-176 | — |
| 63 | C₆H₅ | | | 3-CH₃—1-pyrazolyl and 5-CH₃—1-pyrazolyl | CONH₂ | — | A |
| 64 | C₆H₅ | | | 3-CH₃—1-pyrazolyl and 5-CH₃—1-pyrazolyl | CN | — | A |
| 65 | 3,4-OCH₂O.C₆H₃ | | | 1-pyrazolyl | CO₂CH₃ | 150-151 | B |
| 66 | 3,4-OCH₂O.C₆H₃ | | | 1-pyrazolyl | CONH₂ | 162-163 | B |
| 67 | 3,4-OCH₂O.C₆H₃ | | | 1-pyrazolyl | CN | 184-187 | B |
| 68 | 3,4-OCH₂O.C₆H₃ | | | 1-pyrazolyl | CSNH₂ | 156-158 | — |
| 69 | 3,4-OCH₂O.C₆H₃ | | | 1-(1,2,4-triazolyl) | CONH₂ | 211-214 | B |
| 70 | 3,4-OCH₂O.C₆H₃ | | | 1-(1,2,4-triazolyl) | CN | 170-172 | B |
| 71 | 3-Cl.C₆H₄ | | | 1-(1,2,3,4-tetrazolyl) | CN | gum | A |
| 72 | 4-Cl.C₆H₄ | | | 1-pyrazolyl | CN | 157-159 | A |
| 73 | 4-CH₃.C₆H₄ | | | 1-pyrazolyl | CN | 166-168 | A |
| 74 | 4-CH₃.C₆H₄ | | | 1-pyrazolyl | CONH₂ | 169-171 | A |
| 75 | 4-Cl.C₆H₄ | | | 1-pyrazolyl | CONH₂ | 180-182 | A |
| 76 | 4-Br.C₆H₄ | | | 1-pyrazolyl | CN | 155-157 | A |
| 77 | 4-Br.C₆H₄ | | | 1-pyrazolyl | CONH₂ | 175-178 | A |
| 78 | 4-CH₃O.C₆H₄ | | | 1-pyrazolyl | CN | 130-132 | B |
| 79 | 4-CH₃O.C₆H₄ | | | 1-pyrazolyl | CONH₂ | 174-176 | B |
| 80 | 3-F,4-CH₃.C₆H₃ | | | 1-pyrazolyl | CONH₂ | 144-145 | A |
| 81 | 3,F—R-CH₃.C₆H₃ | | | 1-pyrazolyl | CN | 155 | A |
| 82 | 3,F—4-CH₃.C₆H₃ | | | 1-pyrazolyl | CONH₂ | 189-190 | B |
| 83 | 3,F—4-CH₃O.C₆H₃ | | | 1-pyrazolyl | CN | 158-159 | B |
| 84 | 4-Cl—3,F—C₆H₃ | | | 1-pyrazolyl | CN | 149-150 | A |
| 85 | 4-Br—3,F.C₆H₃ | | | 1-pyrazolyl | CN | 165-168 | A |
| 86 | 4-Br—3,F.C₆H₃ | | | 1-pyrazolyl | CONH₂ | 174-176 | B |
| 87 | 4,Me—3,Br.C₆H₃ | | | 1-pyrazolyl | CN | 175-177 | A |
| 88 | 4,Cl—3,Br.C₆H₃ | | | 1-pyrazolyl | CN | 170-175 | A |

In the foregoing table compound Nos. 67, 72, 73, 76, 78, 81 and 84 are particularly useful fungicides.

The structural formula given above is believed to be the one which best represents the structure of the compounds of the invention. For some compounds within the scope of the formula (I) it may be possible in principle for tautomeric forms of the compound to exist, in which a hydrogen atom is transposed from the position in which it is shown in formula (I) to another part of the molecule, and the chemical bonds between the atoms of the molecule are consequently rearranged. The structural formula (I) is intended to represent and include such tautomeric forms, insofar as they may exist. It will be noted that the formula (I) includes an asymmetric carbon atom (the one to which the groups X an Y are attached) and the molecule is therefore capable in principle of existing in two optically isomeric forms (D and L forms). The present invention includes the separate D and L forms of the compounds as well as mixtures of the D and L forms in all proportions. As normally prepared by chemical synthesis the compounds are obtained as mixtures of equal proportions of the D and L forms (i.e. racemic mixtures). Methods of separating racemic mixtures into the D and L forms are well known in the art.

The structural formula (I) is also intended to include any physically distinguishable modifications of the compounds which may arise, for example, from different ways in which the molecules are arranged in a crystal lattice, or from the inability of parts of the molecules to rotate freely in relation to other parts, or from geometrical isomerism, or from intra-molecular or inter-molecular hydrogen bonding, or otherwise.

The invention further provides processes for preparing compounds of formula (I) above. One such process is outlined in Scheme A below.

Scheme A

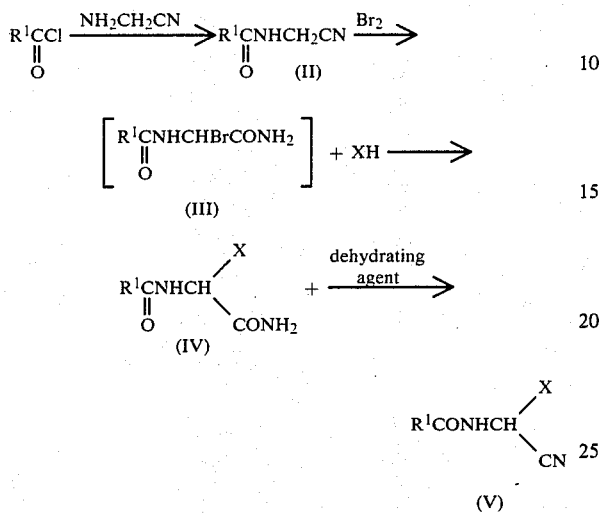

According to Scheme A, an acid chloride R¹COCl is reacted with aminoacetonitrile to give the acylaminoacetonitrile (II). This is treated with bromine to give the unstable brominated intermediate (III). This reaction is conveniently carried out in a solvent, for example acetic acid. The reaction is carried out at a temperature in the range from 10° to 50° C., preferably at room temperature. The brominated intermediate (III), being unstable, is used shortly after its preparation has been completed. The brominated compound (III) is reacted with a 5-membered heteroaromatic compound, designated in Scheme A by the symbol XH. The reaction may be carried out in the presence of an acid acceptor. Examples of acid acceptors include tertiary amines, for example triethylamine, dimethylaniline, and pyridine. The reaction is preferably carried out in a solvent or diluent for the reactants. Pyridine may be used both as solvent and acid acceptor. The reaction is generally exothermic and cooling may be desirable to moderate the vigour of the reaction, which could lead to decomposition of the reactants. Preferably the reaction is carried out at a temperature of less than 100° C., for example at or below 30° C. The amide (IV) produced in the reaction may be isolated by conventional methods, for example by diluting the reaction mixture with a solvent in which the amide (IV) is insoluble or only slightly soluble, and thereby precipitating the product. In the final stage of Scheme A, the amide (IV) is treated with a dehydrating agent to convert the amide to the nitrile (V). Various dehydrating agents are known in the art for converting amides to nitriles. The conversion of (IV) to the nitrile (V) may be accomplished, for example, by treatment of a solution of (IV) in pyridine with trifluoroacetic anhydride. This reaction is generally exothermic and is preferably carried out below 0° C., for example at a temperature in the range from −20° to −10° C. The product (V) may be isolated from the reaction mixture by conventional methods.

A further process for preparing compounds according to the invention is outlined in Scheme B below.

Scheme B

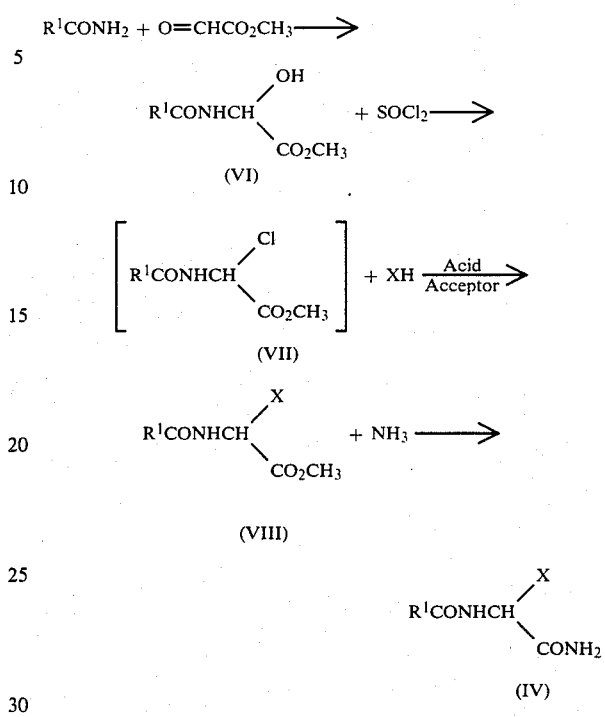

According to Scheme B, an amide R¹CONH₂ is reacted with methyl glyoxylate to give the hydroxy-ester (VI). This reaction is conveniently carried out in a solvent and may be accelerated by heating. Examples of solvents include liquid hydrocarbons, for example toluene and the xylenes. The reaction may be carried out at temperatures in the range from 50° to 120° C. and preferably above 100° C. The hydroxy amide product (VI) may be isolated by removal of the solvent. The hydroxy amide (VI) is then converted to the unstable chloro-compound (VII) by treatment with thionyl chloride. Conveniently the reaction is carried out in an excess of thionyl chloride as solvent. The reaction proceeds at moderate temperatures (for example, temperatures in the range from 15°–50° C.). The chloro-compound (VII) may be isolated by removal of the excess of thionyl chloride under reduced pressure. The chloro-compound (VII) is then reacted with a 5-membered heteroaromatic compound XH in the presence of an acid acceptor. Examples of acid acceptors include tertiary amines, for example triethylamine, pyridine, and dimethylaniline. Conveniently the reaction may be performed using an excess of pyridine as both solvent and acid acceptors. The reaction proceeds at moderate temperatures (i.e. temperatures in the range 15°–10° C.).

The ester product (VIII) from the foregoing reaction is then reacted with ammonia to give the amide intermediate (IV) referred to in Scheme A above. The reaction with ammonia is conveniently carried out in a solvent, for example a lower alkanol (eg. methanol or ethanol) or an ether (eg. diethyl ether or tetrahydrofuran). The reaction may be carried out by saturating the solution of the ester (VIII) with ammonia at a lowered temperature (eg. −50° to −10° C.) and subsequently allowing the mixture to warm to room temperature. The amide (IV) so obtained may then be converted if desired to the corresponding nitrile as described in Scheme A.

Compounds according to the invention in which Y is a —CSNH$_2$ group may be prepared by treating the corresponding compounds in which Y is a —CN group with hydrogen sulphide. This reaction is conveniently carried out by passing gaseous hydrogen sulphide into a pyridine solution of the compound in which Y is a CN group. A small amount of triethylamine may be added as a catalyst for the reaction. The product may be isolated for example by diluting the pyridine solution with water and collecting the precipitated product.

In another aspect the invention provides a process of inhibiting the growth of unwanted plants, which comprises applying to the plants, or the locus thereof, a phytotoxic amount of a compound of the formula (I) as hereinbefore defined. The amount of the compound may vary, depending upon the identity of the particular compound chosen and the plant species whose growth is to be inhibited, but in general amounts of from 0.005 to 5.0 kilograms per hectare will be suitable; usually the amount will be from 0.2 to 1.0 kilograms per hectare. The skilled worker in the herbicide art will readily be able to establish appropriate application rates by standard procedures without undue experimentation.

The compounds of the invention are relatively less toxic towards certain crop plants than they are towards other plant species; accordingly, there is the possibility of using the compounds for selective weed control in these crops. Examples of such crops include wheat and maize.

The compounds used in the process of the invention are preferably applied in the form of a composition, in which the active ingredient is mixed with a carrier comprising a solid or liquid diluent. In another aspect, therefore, the invention provides a herbicidal composition, comprising as an active ingredient a compound of the formula (I) as hereinbefore defined, in admixture with a solid or liquid diluent. Preferably the composition also comprises a surface-active agent.

The solid compositions of the invention may be for example, in the form of dusting powders, or may take the form of granules. Suitable solid diluents include, for example, kaolin, bentonite, kieselguhr, dolomite, calcium carbonate, talc, powdered magnesia, and Fuller's earth.

Solid compositions may also be in the form of dispersible powders or grains comprising in addition to the active ingredient, a wetting agent to facilitate the dispersion of the powder or grains in liquids. Such powders or grains may include fillers, suspending agents and the like.

Liquid compositions include aqueous solutions, dispersions and emulsions containing the active ingredient preferably in the presence of one or more surface active agents. Water or organic liquids may be used to prepare solutions, dispersions, or emulsions of the active ingredient. The liquid compositions of the invention may also contain one or more corrosion inhibitors for example lauryl isoquinolinium bromide.

Surface active agents may be of the cationic, anionic or non-ionic type. Suitable agents of the cationic type include for example quaternary ammonium compounds, for example cetyltrimethyl ammonium bromide. Suitable agents of the anionic type include for example soaps, salts of aliphatic mono-esters of sulphuric acid, for example sodium lauryl sulphate; and salts of sulphonated aromatic compounds, for example dodecylbenzenesulphonate, sodium, calcium and ammonium lignosulphonate, butylnaphthalene sulphonate, and a mixture of the sodium salts of diisopropyl- and triisopropylnaphthalenesulphonic acid. Suitable agents of the non-ionic type include, for example, the condensation products of ethylene oxide with fatty alcohols such as oleyl alcohol and cetyl alcohol, or with alkyl phenols such as octylphenol, nonylphenol, and octylcresol. Other non-ionic agents are the partial esters derived from long chain fatty acids and hexitol anhydrides, for example sorbitol monolaurate; the condensation products of the said partial esters with ethylene oxide and the lecithins.

The compositions which are to be used in the form of aqueous solutions, dispersions or emulsions are generally supplied in the form of concentrate containing a high proportion of the active ingredient, the concentrate being diluted with water before use. These concentrates are usually required to withstand storage for prolonged periods and after such storage to be capable of dilution with water in order to form aqueous preparations which remain homogenous for a sufficient time to enable them to be applied by conventional spray equipment.

The compositions of the invention may contain, in addition to carriers and surface-active agents, various other constituents to increase their usefulness. They may contain, for example, buffering salts to maintain the pH of the composition within a desired range; antifreeze agents, for example urea or propylene glycol; adjuvants, for example, oils and humectants; and sequestrants, for example citric acid and ethylenediaminetetracetic acid, which help to prevent the formation of insoluble precipitates when the compositions are diluted with hard water. Aqueous dispersions may contain anti-settling agents and anti-caking agents. The compositions may in general contain a dye or pigment to impart a characteristic colour. Agents for increasing viscosity may be added to reduce the formation of fine droplets during spraying, and thereby reduce spray drift. Other additives useful for particular purposes will be known to those skilled in the formulation art.

In general concentrates may conveniently contain from 10 to 85% and preferably from 25 to 60% by weight of active ingredient. Dilute preparations ready for use may contain varying amounts of the active ingredient, depending upon the purpose for which they are to be used; however, dilute preparations suitable for many uses contain between 0.01% and 10% and preferably between 0.1% and 1% by weight of the active ingredient.

In another aspect the invention provides a process of inhibiting the growth of fungi on plants, which comprises applying to the plants, to the seed of the plant, or to the locus of the plant or seed, a fungicidally effective amount of a compound of the formula (I) as hereinbefore defined. The amount of the compound may vary, depending upon the identity of the particular compound chosen, the fungal species whose growth is to be inhibited, and the plant or locus involved.

In a still further aspect the invention provides a process for combating fungi which comprises applying to the fungi, or the locus thereof, a fungicidally effective amount of a compound as herein before defined.

The skilled worker in the fungicide art will readily be able to establish appropriate application rates by standard procedures without undue experimentation. The compounds used in the process and compositions of the invention are preferably applied in the form of a composition, in which the active ingredient is mixed with a carrier comprising a solid or liquid diluent. In another aspect, therefore, the invention provides a fungicidal composition, comprising as an active ingredient a compound of the formula (I) as hereinbefore defined, in admixture with a solid or liquid diluent. Preferably the composition also comprises a surface-active agent.

The substituted amide derivatives, and compositions containing them, are variously active against a wide range of fungal diseases, particularly, for example against those produced by pathogens belonging to the fungal class Oomycetes. Some of the pathogens controlled are listed below:

(a) *Plasmopara viticola* (causing downy mildew on vines)

(b) *Phytophthora infestans* (causing late blight on potatoes and tomatoes)

(c) *Pythium ultimum* (causing pre-emergence damping-off of mustard and other crops)

Other Oomycete pathogens against which activity has been demonstrated or can be expected include *Aphanomyces euteiches, Pythium aphanidermatum, P. debaryanum, Phytophthora parasitica, P. megasperma, P. cactorum, P. cinnamomi* and other species of Phytophthora, *Pseudoperonospora cubensis, Peronospora hyoscyami* and *Bremia lactucae* and other species of these genera.

The amide derivatives may also be useful as industrial fungicides, eg. in the prevention of fungal attack on wood, hides, leather and especially paint films.

The amide derivatives may be used as such for antifungal purposes but are more conveniently formulated into compositions for such usage.

The invention also provides fungicidal compositions comprising as active ingredient an amide derivative as defined in any of the paragraphs above.

The amide derivatives and compositions containing them can be used to combat plant fungi and treat plants or seeds in a number of ways, for example they can be applied, formulated or unformulated, directly to the foliage of a plant which is infected or likely to become infected, or they can be applied also to bushes and trees, to soil or to other medium in which plants, bushes or trees are growing or to be planted, or they can be sprayed on, dusted on or applied as a cream or paste formulation. Application can be to any part of the plant, bush or tree, for example to the foliage, stems, branches, seeds or roots, or to the soil surrounding the roots.

The terms "combating" and "treatment" as used herein embrace all the foregoing modes of application and the term "plant" includes seedlings, bushes and trees. Furthermore, the method of the invention includes protectant, prophylactic and eradicant treatment.

The derivatives are preferably used for agricultural and horticultural purposes in the form of compositions. The type of composition used in any instance will depend upon the particular purpose envisaged.

The compositions may be in the form of dusting powders or granules, for example ordinary grains or "slow release" granules wherein the active ingredient is mixed with a solid diluent or carrier, for example, kaolin, bentonite, kieselguhr, dolomite, calcium carbonate, talc, powdered magnesia, Fuller's earth, gypsum, Hewitt's earth, diatomaceous earth and China clay. Compositions for dressing seed may, for example, comprise an agent (for example a mineral oil) for assisting the adhesion of the composition to the seed.

The compositions may also be in the form of dispersible powders or grains comprising a wetting agent to facilitate the dispersion in liquids of the powder or grains which may contain also fillers and suspending agents.

The aqueous dispersion of emulsions may be prepared by dissolving the active ingredient(s) in an organic solvent which may contain wetting, dispersing or emulsifying agent(s) and then adding the mixture so obtained to water which may also contain wetting, dispersing or emulsifying agent(s). Suitable organic solvents are ethylene dichloride, isopropyl alcohol, propylene glycol, diacetone alcohol, toluene, kerosene, methylnaphthalene, xylenes and trichloroethylene.

The compositions for spraying may also be in the form of aerosols wherein the formulation is held in a propellant, eg. fluorotrichloromethane or dichlorodifluoromethane.

By including suitable additives, for example additives for improving the distribution, adhesive power and resistance to rain on treated surfaces, the different compositions can be better adapted for various utilities.

The derivatives can be used in smoke generators and also as mixtures with fertilisers (eg. nitrogen- or phosphorus-containing fertilisers). Compositions comprising only granules of fertiliser incorporating, for example coated with, the derivative, are preferred.

The invention therefore also provides a fertiliser composition comprising the derivative and a fertiliser.

The compositions may also be in the form of liquid preparations for use as dips or sprays which are generally aqueous dispersions or emulsions containing the active ingredient in the presence of one or more surface active agent(s), dispersing agent(s), emulsifying agent(s) or anionic or non-ionic agents. Suitable cationic agents are quaternary ammonium compounds for example, cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropylnaphthalene sulphonates).

Suitable non-ionic agents are the condensation products of ethylene oxide with fatty alcohols such as oleyl alcohol or cetyl alcohol, or with alkyl phenols such as octylphenol, nonylphenol and octylcresol. Other nonionic agents are the partial esters derived from long chain fatty acids and hexitol anhydrides, the condensation products of the said partial esters with ethylene oide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), the concentrate to be diluted with water before use. These concentrates often should be able to withstand storage for prolonged periods and after such form aqueous preparations which remain homogeneous for sufficient time to enable them to be applied by conventional spray equipment. The concentrates may conveniently contain 10–85%, generally 25–60%, by weight of the active ingredient(s). When diluted to form aqueous preparations, such preparations may contain varying amounts of the active ingredient(s) depending upon the intended purpose, but an aqueous preparation containing 0.0005% or 0.01% to 10% by weight of active ingredient(s) may be used.

The compositions of this invention can comprise also other compound(s) having biological activity, eg. compounds having similar or complementary fungicidal activity or compounds having plant growth regulating, herbicidal or insecticidal activity.

The other fungicidal compound can be for example one which is capable of combating ear diseases of cereals (eg. wheat) such as Septoria, Gibberella and Helminthosporium spp., seed and soil borne diseases and downy and powdery mildews on grapes and powdery mildew and scab on apple etc. These mixtures of fungicides can have a broader spectrum of activity than the compound of general formula (I) alone; further the other fungicide can have a synergistic effect on the fungicidal activity of the compound of general formula (I). Examples of the other fungicidal compound are imazalil, benomyl, carbendazim, thiophanate-methyl, captafol, captan, sulphur, triforine, dodemorph, tridemorph, pyrazophos, furalaxyl, ethirimol, dimethirimol, bupirimate, chlorothalonil, vinclozolin, procymidone, iprodione, metalaxyl, forsetyl-aluminium, carboxin, oxycarboxin, fenarimol, nuarimol, fenfuram, methfuroxan, nitrotal-isopropyl, triadimefon, thiabendazole, etridiazole, triadimenol, biloxazol, dithianon, binapacryl, quinomethionate, guazitine, dodine, fentin acetate, fentin hydroxide, dinocap, folpet, dichlofluanid, ditalimphos, kitazin, cycloheximide, dichlobutrazol, a dithiocarbamate, a copper compound, a mercury compound, 1-(2-cyano-2-methoxyiminoacetyl)-3-ethyl urea, fenapanil, ofurace, propiconazole, etaconazole and fenpropemorph.

The compounds of general formula (I) can be mixed with soil, peat or other rooting media for the protection of plants against seed-borne, soil-borne or foliar fungal diseases.

Suitable insecticides are pirimor, croneton, dimethoate, metasystox and förmothion.

Examples of suitable plant growth regulating compounds are the gibberellins (eg. GA$_3$, GA$_4$ or GA$_7$), the auxins (eg. indoleacetic acid, indolebutyric acid, naphthoxyacetic acid or naphthylacetic acid), the cytokinins (eg. kinetin, diphenylurea, benzimidazole, benzyladenine or benzylaminopurine), phenoxyacetic acids (eg. 2,4-D or MCPA), substituted benzoic acids (eg. triiodobenzoic acid), morphactins (eg. chlorfluorecol), maleichydrazide, glyphosate, glyphosine, long chain fatty alcohols and acids, dikegulac, fluoridamid, mefluidide, substituted quaternary ammonium and phosphonium compounds (eg. chlormequat or chlorphonium), ethepon, carbetamide, methyl-3,6-dichloranisate, daminozide, asulam, abscissic acid, isopyrimol, 1-(4-chlorophenyl)-4,6-dimethyl-2-oxo-1,2-dihydropyridine-3-carboxylic acid, hydroxybenzonitriles (eg. bromoxynil), difenzoquat, benzoylprop-ethyl 3,6-dichloropicolinic acid.

The invention is illustrated by the following Examples, in which unless otherwise stated all parts are by weight and all temperatures in degrees Centigrade. The Examples that describe chemical synthesis give details in some cases of the nuclear magnetic resonance (NMR) spectra of the compounds. The information given is the chemical shift ($\delta$) for each peak in the spectrum together with a symbol to indicate the nature of the peak, as follows:

s (singlet); d (doublet); m (multiplet); q (quartet); t (triplet). The solvent used was fully deuterated dimethyl sulphoxide (DMSO-d$_6$) or deuterochloroform (CDCl$_3$).

Details of infra-red spectra are also given; these are indicated by the symbol $\gamma$.

EXAMPLE 1

This Example illustrates the preparation of 2-(3-chlorobenzoylamino)-2-[1-(1,2,4-triazolyl)]acetonitrile (Compound 1 of Table 1) by the process of Scheme A.

(a) Preparation of 2-Bromo-2-[3-chlorobenzoylamino]acetamide

To a stirred suspension of 3-chlorobenzoylamino acetonitrile (11.65 g) (prepared from 3-chlorobenzoylchloride and aminoacetonitrile) in glacial acetic acid (50 ml) was added all at once bromine (9.6 g). Following the mild exotherm the solution was stirred for a further 30 minutes, when the solid was filtered off, washed with dry ether, and then placed under high vacuum for 15 minutes. This gave 12.4 g (71%) of the bromoamide, which was used immediately for the next stage.

(b) Preparation of 2-(3-Chlorobenzoylamino)-2-(1-triazoyl)acetamide

To a cooled (water bath) and stirred solution of 1,2,4-triazole (2.94 g) in anhydrous pyridine (100 ml) protected from moisture, was added in portions the foregoing bromoamide (12.4 g) at such a rate that the temperature of the mixture did not exceed 30°. Following the addition the mixture was kept overnight at room temperature when it was heated to 70° until such time as the solid had dissolved. On cooling to room temperature the mixture was treated with water (500 ml) and stirred for 30 minutes. The precipitated solid was separated, dried, and crystallized from pyridine-ether as a white microcrystalline powder (8.1 g; 68%), m.p. 205°–206°.

Found: C, 47.72; H, 3.72; N, 24.51. C$_{11}$H$_{10}$ClN$_5$O$_2$ Requires: C, 47.24; H, 3.6; N, 25.04%. $\delta$ (DMSO-d$_6$): 6.9 (1H,d), ca. 7.8 (7H,m), 8.75 (1H,s), 10 (1H,d).

(c) Preparation of 2-(3-Chlorobenzoylamino-2-(1-triazolyl)acetonitrile

The foregoing triazolylacetamide (7.15 g) was dissolved in anhydrous pyridine (150 ml) with gentle warming. To the cooled (−20°) solution protected from moisture was added with stirring trifluoroacetic anhydride (11.0 g) at such a rate that the temperature of the mixture did not exceed −10°. Following the addition the mixture was allowed to come to room temperature and then poured into water (300 ml). The solution was extracted with ether and (3×100 ml) the combined ethereal extracts dried (MgSO$_4$) and evaporated to give a solid. This was crystallised from ethyl acetate-petrol to give the product as a colourless microcrystalline solid (3.32 g; 50%), mp. 157°–159°.

Found: C, 50.67; H, 3.22; N, 26.23. C$_{11}$H$_8$ClN$_5$O Requires: C, 50.49; H, 3.08; N, 26.76%. $\delta$ (DMSO-d$_6$): 7.9 (5H,m), 8.3 (1H,s), 8.9 (1H,s), 10.9 (1H,d).

$\gamma$ (Nujol): 3300, 1665, 1510 cm$^{-1}$.

EXAMPLE 2

This Example illustrates the preparation of 2-(3,5-dimethylbenzoylamino)-2-(1-pyrazolyl)acetonitrile (Compound 14 of Table 1) by the process of Scheme B.

(a) Preparation of Methyl 2-(3,5-Dimethylbenzoylamino)-2-(1-pyrazolyl)acetate (Compound 10 of Table 1)

Crude methyl 2-(3,5-dimethylbenzoylamino)-2-hydroxy acetate was prepared by refluxing equimolar proportions of 3,5-dimethylbenzamide and methyl glyoxylate in toluene and then removing the solvent under reduced pressure. The hydroxyamide thus obtained (3 g) was dissolved in thionyl chloride (25 ml) and kept at room temperature for 1 hour. The excess of thionyl chloride was removed under reduced pressure and the remaining oil triturated with n-hexane to give a reactive and unstable white solid. The solid was added in portions to a solution of pyrazole (0.7 g) in anhydrous pyridine (30 ml) and the mixture kept at room temperature for 4 days. Water (200 ml) was then added to the mixture and the product separated, dried and crystallized from carbon tetrachloride-cyclohexane. Yield: 1.51 g, mp. 163°–165°.

Found: C, 62.45; H, 5.89; N, 14.43. $C_{15}H_{17}N_3O_3$ Requires: C, 62.71; H, 5.96; N, 14.62%. δ ($CDCl_3$): 2.35 (6H,s), 3.8 (3H,s), 6.26 (1H,m), 6.7 (1H,d), 7.15–7.8 (6H,m).

(b) Preparation of 2-(3,5-Dimethylbenzoylamino)-2-(1-pyrazolyl)acetamide (Compound 13 of Table 1)

The foregoing ester (1 g) was suspended in ethanol (30 ml) and tetrahydrofuran (5 ml) and cooled to −50° at which temperature it was saturated with ammonia. The mixture was allowed to come to room temperature and then evaporated under reduced pressure. The residue solid was crystallised from ethyl acetate to give the product (700 mg), mp. 193°–195°.

Found: C, 62.02; H, 5.99; N, 20.5. $C_{14}H_{16}N_4O_2$ Requires: C, 61.75; H, 5.92; N, 20.57%. δ ($CDCl_3$-DMSO-$d_6$): 2.25 (6H,s), 6.35 (1H,m), 6.9 (1H,d), 7.2–8.0 (7H,m), 8.65 (1H,d).

(c) Preparation of 2-(3,5-Dimethylbenzoylamino)-2-(1-pyrazolyl)acetonitrile (Compound 14 of Table 1)

The foregoing amide (652 mg) was converted to the nitrile using trifluoroacetic anhydride-pyridine as described in Example 1 to give the product as a buff microcrystalline powder (350 mg), mp. 180°–183°

Found: C, 65.56; H, 5.5; N, 21.59. $C_{14}H_{14}N_4O$ Requires: C, 66.13; H, 5.55; N, 22.03%. δ ($CDCl_3$): 2.35 (6H,s), 6.3 (1H,m), 7.1–7.9 (6H,m), 10.2 (1H,d).

EXAMPLE 3

This Example illustrates the preparation of 2-benzamido-2-(1-pyrazolyl)acetonitrile, using the method of Scheme A, and using dimethylformamide and phosphorus oxychloride as the dehydrating agent.

(a) Preparation of 2-benzamido-2-(1-pyrazolyl)acetamide (Compound 34 of Table 1).

This compound was prepared from 2-benzamidoacetonitrile by bromination and treatment of the unstable bromo compound (formula III, $R^1=C_6H_5$) with pyrazole. The product, recrystallised from ethyl acetate, had a melting point of 183°–186° C.

(b) Preparation of 2-benzamido-2-(1-pyrazolyl)acetonitrile (Compound 35 of Table 1).

Phosphorus oxychloride (1.2 g) was added dropwise to stirred anhydrous dimethylformamide (10 ml) maintained at 0°–5° and protected from moisture. Following the addition, the cold (0°–5°) mixture was added dropwise and with stirring to a cooled (0°–5°) solution of the product from paragraph (a) (1.0 g) in anhydrous dimethylformamide (10 ml) at such a rate that the temperature of the mixture did not exceed 5°. After addition was complete, the mixture was poured into water (50 ml) and the product collected, washed with water, and dried. Crystallisation from chloroform gave the product as a white microcrystalline powder (0.4 g), m.p. 169°–174°.

δ ($CDCl_3$-DMSO-$d_6$): 6.25 (m,1H), 7.4–8.0 (m,8H) 10.3 (s, broad, 1H).

EXAMPLE 4

This Example illustrates the herbicidal properties of compounds of Table 1. The compounds were submitted to herbicide tests as described below.

Each compound was formulated for test by mixing an appropriate amount of it with 5 ml of an emulsion prepared by diluting 160 ml of a solution containing 21.8 grams per liter of Span 80 and 78.2 grams per liter of Tween 20 in methylcyclohexanone to 500 ml with water. Span 80 is a Trade Mark for a surface-active agent comprising sorbitan monolaurate. Tween 20 is a Trade Mark for a surface-active agent comprising a condensate of 20 molar proportions of ethylene oxide with sorbitan monolaurate. The mixture of the compound and the emulsion was then shaken with glass beads and diluted to 40 ml with water. The spray composition so prepared was sprayed on to young pot plants (post-emergence test) of the species named in Table 2 below, at a rate equivalent to 1000 liters per hectare. Damage to plants was assessed 14 days after spraying by comparison with untreated plants, on a scale of 0 to 5 where 0 is 0 to 20% damage and 5 is complete kill. In the table of results, a dash (-) means that no test was made.

A test was also carried out to detect pre-emergence herbicidal activity. Seeds of the test species were placed on the surface of fibre trays of soil and were sprayed with the compositions at the rate of 1000 liters per hectare. The seeds were then covered with further soil. Three weeks after spraying, the seedlings in the sprayed fiber trays were compared with the seedlings in unsprayed control trays, the damage being assessed on the same scale of 0 to 5.

The results of the tests are given in Table 2 below.

TABLE 2

| COMPOUND NO | RATE OF APPLICATION kg/ha | PRE- OR POST-EMERGENCE APPLICATION | Sb | Rp | Ct | Sy | Mz | Ww | Rc | Sn | Ip | Am | Pi | Ca | Ga | Xs | Ab | Co | Ot/Av | Dg | Al | St | Ec | Sh | Ag | Cn |
|---|---|---|---|---|---|---|---|---|---|---|---|---|---|---|---|---|---|---|---|---|---|---|---|---|---|---|
| 1 | 1.0 | Pre | 4 | 3 | 2 | 2 | 2 | 3 | 1 | 4 | 2 | 4 | — | 2 | — | 3 | 3 | 0 | — | 4 | 4 | 4 | 3 | 3 | 0 | — |
|   |   | Post | 1 | 0 | 0 | 2 | 2 | 2 | 0 | 3 | 3 | — | 3 | 2 | — | 2 | 0 | — | 3 | 3 | 3 | 3 | 2 | 4 | 2 | — |
| 2 | 1.0 | Pre | 3 | 3 | 1 | 1 | 0 | 2 | 1 | 3 | 3 | 4 | 4 | 4 | 3 | 2 | 2 | 0 | 3 | 5 | 3 | 4 | 4 | 4 | 0 | — |
|   |   | Post | 1 | 1 | 1 | 3 | 3 | 2 | 1 | 2 | 1 | 3 | 2 | 5 | 1 | 2 | 5 | 3 | 2 | 3 | 5 | 3 | 0 | 1 | 2 | 3 |
| 4 | 0.2 | Pre | 5 | 5 | 4 | 4 | 3 | 2 | 4 | 4 | 4 | 4 | — | 4 | — | 5 | 5 | 4 | 4 | 5 | 5 | 5 | 5 | 4 | 5 | 3 |
|   |   | Post | 3 | 2 | 2 | 5 | 4 | 5 | 3 | 4 | 4 | 3 | — | 2 | 3 | 2 | 5 | 2 | 5 | 3 | 5 | 3 | 4 | 3 | 4 | 2 |
| 4 | 0.05 | Pre | 5 | 4 | 3 | 4 | 4 | 3 | 4 | 4 | 3 | 5 | — | 4 | — | 5 | 5 | 3 | 5 | 4 | 5 | 5 | 5 | 3 | 2 | 2 |
| 6 | 1.0 | Post | 5 | 5 | 4 | 5 | 4 | 5 | 5 | 4 | 4 | 5 | — | 5 | 5 | 2 | 5 | 5 | 5 | 5 | 5 | 5 | 5 | 4 | 5 | 5 |
| 12 | 0.2 | Pre | 3 | 3 | 3 | 2 | 4 | 4 | 4 | 2 | 2 | 2 | — | 3 | 3 | 3 | 2 | 2 | 4 | 5 | 4 | 4 | 5 | 3 | — | 4 |
|   |   | Post | 5 | 5 | 2 | 2 | 3 | 4 | 3 | 4 | 4 | 3 | — | 1 | — | 2 | 2 | 2 | 3 | 3 | 5 | 5 | 5 | 2 | 1 | 2 |
| 13 | 1.0 | Pre | 3 | 3 | 1 | 1 | 2 | 3 | 1 | 2 | 2 | 1 | — | 3 | — | 3 | 0 | 1 | 3 | 2 | 5 | 2 | 4 | 3 | — | 2 |
|   |   | Post | 4 | 3 | 0 | 2 | 1 | 3 | 1 | 4 | 1 | 2 | — | 0 | — | 0 | 4 | 0 | 2 | 2 | 0 | 2 | 0 | 1 | — | 2 |
| 15 | 0.2 | Pre | 1 | 0 | 0 | 1 | 1 | 1 | 0 | 3 | — | — | — | 0 | — | 0 | — | — | 3 | 1 | 0 | 0 | 1 | — | 0 | — |
|   |   | Post | 4 | 5 | 3 | 4 | 3 | 5 | 4 | 4 | 4 | 5 | — | 4 | — | 3 | 3 | 3 | 2 | 3 | 5 | 3 | 5 | 4 | 4 | 3 |
| 18 | 5.0 | Pre | 2 | 2 | 1 | 3 | 2 | 3 | 2 | 3 | 3 | 2 | — | 3 | — | 3 | — | 4 | 4 | 3 | 5 | 3 | 2 | 3 | 2 | 2 |
|   |   | Post | 3 | 3 | 0 | — | 0 | 3 | 3 | 2 | — | 4 | — | 3 | — | 3 | — | 3 | 3 | 3 | 3 | 3 | 3 | 0 | 2 | 2 |
| 19 | 0.2 | Pre | 5 | 4 | 2 | 3 | 3 | 3 | 3 | 5 | — | 5 | — | 5 | 5 | 5 | 4 | — | 4 | 5 | 5 | 5 | 5 | — | 4 | — |
|   |   | Post | 3 | 3 | 2 | 2 | 2 | 3 | 0 | 3 | 3 | 3 | 0 | 3 | — | 2 | — | 3 | 2 | 4 | 2 | 2 | 1 | — | 2 | 0 |
| 20 | 1.0 | Pre | 3 | 2 | 0 | 0 | 0 | 3 | 0 | 2 | 2 | 3 | — | 0 | — | — | — | 2 | 5 | 4 | 3 | 3 | 3 | 0 | 2 | 3 |
|   |   | Post | 3 | 3 | 1 | 2 | 1 | 2 | 1 | 2 | 2 | 3 | — | 3 | — | 2 | 4 | — | 3 | 3 | — | 3 | — | 0 | 3 | — |
| 21 | 0.2 | Pre | 4 | 3 | 2 | 3 | 3 | 4 | 3 | 4 | 4 | 5 | — | 4 | — | 4 | — | 3 | 4 | 4 | 5 | 5 | 5 | 2 | 0 | 2 |
|   |   | Post | 3 | 3 | 3 | 2 | 2 | 3 | — | 3 | 3 | 3 | — | 3 | — | 2 | 3 | 2 | 3 | 3 | 3 | 3 | 2 | — | 3 | 2 |
| 26 | 0.2 | Pre | 5 | 5 | 4 | 4 | 3 | 4 | 5 | 5 | 5 | 5 | — | 4 | 5 | 4 | 5 | 3 | 5 | 5 | 5 | 5 | 5 | 3 | 5 | 3 |
|   |   | Post | 1 | 4 | 3 | 3 | 2 | 1 | 3 | 0 | 2 | 3 | — | 3 | 3 | 2 | 3 | 1 | 3 | 3 | 2 | 3 | 3 | 1 | — | 2 |
| 28 | 0.2 | Pre | 4 | 4 | 2 | 2 | 0 | 3 | 0 | 5 | 2 | 5 | — | 4 | — | 0 | 4 | 1 | 4 | 4 | 5 | 5 | 3 | 2 | 2 | 2 |
|   |   | Post | 0 | 1 | 1 | 1 | 0 | 1 | 1 | 0 | 0 | 3 | 0 | 3 | — | 0 | — | 0 | 0 | 3 | — | 2 | — | — | 2 | — |
| 39 | 0.05 | Pre | 3 | 3 | 2 | 2 | 0 | 3 | 1 | 3 | 2 | 3 | — | 3 | — | — | 4 | 2 | 4 | 3 | 3 | 3 | 4 | 2 | 0 | — |
| 39 | 1.0 | Post | 3 | 3 | 4 | 3 | 3 | 3 | 5 | 4 | 4 | 4 | — | — | — | 3 | 5 | 3 | 5 | 4 | 5 | 5 | 5 | 5 | 2 | 2 |
| 40 | 0.05 | Pre | 4 | 4 | 3 | 4 | 4 | 3 | 3 | 4 | 3 | 3 | 0 | 4 | — | — | 4 | 3 | 4 | 4 | 4 | 5 | 5 | 3 | 3 | 4 |
| 40 | 1.0 | Post | 3 | 3 | 2 | 3 | 3 | 4 | 2 | 4 | 3 | 3 | 0 | 3 | — | 3 | 3 | 3 | 3 | 3 | 3 | 3 | 3 | 3 | 3 | 2 |
| 41 | 1.0 | Pre | 4 | 4 | 2 | 4 | 3 | 3 | 4 | 4 | 4 | 5 | 2 | 4 | — | 3 | 4 | 3 | 5 | 4 | 5 | 5 | 5 | 3 | 5 | 4 |
|   |   | Post | 3 | 4 | 3 | 3 | 3 | 3 | 0 | 4 | 3 | 3 | 3 | 3 | — | 2 | 3 | 3 | 3 | 4 | 3 | 3 | 2 | 2 | 2 | 0 |
| 44 | 1.0 | Pre | 4 | 3 | 2 | 4 | 4 | 5 | 5 | 3 | 2 | 5 | 2 | 5 | — | — | 3 | 4 | 5 | 4 | 5 | 5 | 5 | 3 | 5 | 2 |
|   |   | Post | 4 | 3 | 3 | 2 | 2 | 3 | 4 | 3 | 2 | 3 | 0 | 3 | — | 2 | 4 | 3 | 3 | 5 | 4 | 5 | 5 | 2 | 3 | 4 |
| 46 | 1.0 | Pre | 4 | 4 | 2 | 5 | 3 | 3 | 5 | 4 | 4 | 5 | 4 | 5 | — | 4 | 5 | 4 | 4 | 5 | 4 | 5 | 5 | 5 | 4 | 3 |
|   |   | Post | 3 | 2 | 3 | 3 | 2 | 3 | 3 | 4 | 3 | 3 | 3 | 3 | — | 3 | 3 | 4 | 4 | 4 | 4 | 5 | 4 | — | 3 | 0 |
| 50 | 1.0 | Pre | 3 | 2 | 2 | 4 | 2 | 3 | 4 | 4 | 2 | 3 | 4 | — | — | 3 | — | 3 | 3 | 4 | 5 | 5 | 5 | 3 | 5 | 2 |
|   |   | Post | 0 | — | 2 | 2 | 2 | — | 0 | — | 4 | — | 3 | 1 | — | — | — | 0 | 1 | 3 | — | 2 | — | — | 3 | — |
| 58 | 0.2 | Pre | 3 | 3 | 0 | 1 | 0 | 2 | 1 | 4 | 2 | — | 0 | 1 | — | — | — | — | 2 | 5 | 1 | 2 | 5 | 0 | — | 0 |
| 59 | 2.5 | Post | 1 | 0 | 0 | 0 | 1 | 0 | 0 | 0 | 0 | — | — | — | — | — | 0 | 0 | — | 4 | 3 | 3 | 3 | 0 | 0 | 0 |
| 65 | 1.0 | Pre | 2 | 0 | 1 | 2 | 0 | 1 | 3 | 3 | 2 | — | 0 | — | — | — | — | — | 1 | 4 | — | 3 | 0 | 0 | 2 | 0 |
| 71 | 0.2 | Post | 0 | — | 1 | 3 | 1 | 5 | 0 | 4 | 0 | — | 3 | 0 | — | 3 | 0 | — | 4 | 4 | — | 3 | 4 | — | 0 | 0 |
|   |   | Pre | 4 | 4 | — | — | 0 | 3 | 3 | 4 | 4 | — | 4 | 4 | — | 5 | 4 | 2 | 5 | 5 | 5 | 5 | 5 | 3 | 3 | 3 |
| 72 | 1.0 | Post | 3 | — | 2 | 3 | 3 | 3 | — | 4 | 3 | — | 3 | 3 | — | 3 | 2 | 2 | 4 | 4 | — | 3 | 4 | 3 | 2 | 2 |
|   |   | Pre | 3 | 1 | 3 | 4 | 3 | 3 | 1 | 4 | 4 | — | 3 | 3 | — | 3 | 3 | 4 | 4 | 4 | 5 | 4 | 5 | 3 | 3 | 3 |
| 74 | 5.0 | Pre | 4 | — | 3 | 3 | 1 | 2 | 2 | 3 | 3 | — | 0 | 0 | — | 2 | 4 | 1 | 5 | 3 | 5 | 5 | 5 | 3 | — | — |

Names of test plants in Table 2

| Sb | Sugar beet |
|---|---|
| Rp | Rape |
| Ct | Cotton |
| Sy | Soya Bean |
| Mz | Maize |
| Ww | Winter wheat |
| Rc | Rice |
| Sn | *Senecio vulgaris* |
| Ip | *Ipomoea purpurea* |
| Am | *Amaranthus retroflexus* |
| Pi | *Polygonum aviculare* |
| Ca | *Chenopodium album* |
| Xs | *Xanthium spinosum* |
| Ab | *Abutilon theophrastii* |
| Ga | *Galium aparine* |
| Co | *Cassia obtusifolia* |
| Ot/Av | Oats (cultivated in pre-emergence test and *Avena fatua* (wild oats) in post-emergence test). |
| Dg | *Digitaria sanguinalis* |
| St | *Setaria viridis* |
| Ec | *Echinochloa crus-galli* |
| Sh | *Sorghum halepense* |
| Ag | *Agropyron repens* |
| Cn | *Cyperus rotundus* |
| Al | *Alopecurus myosuriodes* |

EXAMPLE 5

An emulsifiable concentrate was made up by mixing the following ingredients, and stirring the mixture until all the constituents were dissolved.

| Compound No. 1 of Table I | 10% |
|---|---|
| Ethylene dichloride | 40% |
| Calcium dodecylbenzenesulphate | 5% |
| "Lubrol" L | 10% |
| "Aromasol" H | 35% |

EXAMPLE 6

A composition in the form of grains readily dispersible in a liquid, eg. water was prepared by grinding together the first three ingredients in the presence of added water and then mixing in the sodium acetate. The resultant mixture was dried and passed through a British Standard mesh sieve, size 44–100, to obtain the desired size of grains.

| Compound No. 4 of Table I | 50% |
|---|---|
| "Dispersol" T | 25% |
| "Lubrol" APN 5 | 1.5% |
| Sodium acetate | 23.5% |

EXAMPLE 7

The following ingredients were ground together to produce a powder formulation readily dispersible in liquids.

| Compound No. 2 of Table I | 45% |
|---|---|
| "Dispersol" T | 5% |
| "Lissapol" NX | 0.5% |
| "Cellofas" B600 | 2% |
| Sodium acetate | 47.5% |

EXAMPLE 8

The active ingredient was dissolved in acetone and the resultant liquid was sprayed to the granules of China clay. The solvent was then allowed to evaporate to produce a granular composition.

| Compound No. 6 of Table I | 5% |
|---|---|
| China clay granules | 95% |

EXAMPLE 9

A composition suitable for use as a seed dressing was prepared by mixing the three ingredients.

| Compound No. 12 of Table I | 50% |
|---|---|
| Mineral oil | 2% |
| China clay | 48% |

EXAMPLE 10

A dusting powder was prepared by mixing the active ingredient with talc.

| Compound No. 13 of Table I | 5% |
|---|---|
| Talc | 95% |

EXAMPLE 11

A flowable formulation was prepared by ball-milling the constituents set out below and then forming an aqueous suspension of the ground mixture with water.

| Compound No. 15 of Table I | 40% |
|---|---|
| "Dispersol" T | 10% |
| "Lubrol" APN5 | 1% |
| Water | 49% |

EXAMPLE 12

A dispersible powder formulation was made by mixing together the ingredients set out below and then grinding the mixture until all were thoroughly mixed.

| Compound No. 4 of Table I | 25% |
|---|---|
| "Aerosol" OT/B | 2% |
| "Dispersol" A.C. | 5% |
| China clay | 28% |
| Silica | 40% |

EXAMPLE 13

This Example illustrates the preparation of a dispersible powder formulation. The ingredients were mixed and the mixture then ground in a comminution mill.

| Compound No. 6 of Table I | 25% |
|---|---|
| "PERMINAL" BX | 1% |
| "Dispersol" T | 5% |
| Polyvinylpyrrolidone | 10% |
| Silica | 25% |
| China clay | 34% |

EXAMPLE 14

The ingredients set out below were formulated into dispersible powder by mixing then grinding the ingredients.

| | |
|---|---|
| Compound No. 2 of Table I | 25% |
| "Aerosol" OT/B | 2% |
| "Dispersol" A | 5% |
| China clay | 68% |

In Examples 6 to 15 the proportions of the ingredients given are by weight. Similar compositions were prepared using, as active ingredient, Compounds No. 5, 7, 8, 17, 18, 19 and 21.

There now follows an explanation of the compositions or substances represented by the various Trade Marks and Trade Names mentioned above.

| | |
|---|---|
| LUBROL L: | a condensate of nonyl phenol (1 mole) with ethylene oxide (13 moles). |
| AROMASOL H: | a solvent mixture of alkylbenzenes. |
| DISPERSOL T AND AC: | a mixture of sodium sulphate and a condensate of formaldehyde with sodium naphthalene sulphonate. |
| LUBROL APN 5: | a condensate of nonyl phenol (1 mole) with naphthalene oxide (5.5 moles). |
| CELLOFAS B600: | a sodium carboxymethyl cellulose thickener. |

EXAMPLE 15

The compounds were tested against a variety of foliar fungal diseases of plants. The techniques employed were as follows:

The plants were grown in John Innes Potting Compost (No. 1 or 2) in 4 cm diameter mini-pots. A layer of fine sand was placed at the bottom to facilitate uptake of test compound by the roots. The test compounds were formulated either by bead milling with aqueous Dispersol T or as a solution in acetone or acetone/ethanol which was diluted to the required concentration immediately before use. For the foliage diseases suspensions (100 ppm active ingredient) were sprayed on to the foliage and applied to the roots of the same plant via the soil. In the case of *Phytophthora infestans* some chemicals were applied at lower concentrations of active ingredient onto the foliage only. These exceptions are indicated in Table 3.

Sprays were applied to a maximum retention and root drenches to a final concentration equivalent to approximately 40 ppm a.i./dry soil. Tween 20, to give a final concentration of 0.05% was added when the sprays were applied to cereals.

For most of the tests the compound was applied to the soil (roots) and to the foliage (by spraying) one or two days before the plant was inoculated with the disease. After inoculation, the plants were put into an appropriate environment to allow infection to take place and the incubated until the disease was ready for assessment.

In the case of *Pythium ultimum*, the chemicals were applied 1 day after inoculation to artifically infected vermiculite into which mustard seeds had been sown.

TABLE 3

| COMPOUND NUMBER | *PLASMOPARA VITICOLA* (VINE) | *PHYTOPHTHORA INFESTANS* (TOMATO) | *PYTHIUM ULTIMUM* |
|---|---|---|---|
| 1 | 4 | 3* | |
| 2 | 4 | 4 | |
| 3 | 4 | 4 | |
| 4 | 0 | 0 | |
| 5 | 3 | 4 | |
| 11 | 4 | 4 | |
| 12 | 4 | 4 | |
| 14 | 4 | 4 | |
| 17 | 4 | 4 | |
| 18 | 4 | 4 | |
| 20 | 4 | 4 | |
| 24 | 4 | 3* | |
| 26 | 4 | 4 | |
| 27 | 0 | 2 | |
| 28 | 4 | 4* | |
| 29 | 1 | 0 | |
| *Protectant test at 25 ppm. | | | |
| 35 | 4 | 3 | |
| 36 | 4 | 4 | |
| 37 | 4 | 4 | |
| 39 | 3 | 2 | |
| 40 | 4 | 4 | |
| 41 | 3 | 3 | |
| 42 | 4 | 4 | |
| 43 | 4 | 3 | |
| 46 | 4 | 3* | |
| 52 | 0 | | |
| 53 | 2 | 3+ | |
| 58 | 4 | 3 | |
| 60 | 3 | 3 | |
| + Protectant test at 10 ppm. | | | |
| *Protectant and systemic tests at 25 ppm. | | | |
| 61 | 4 | 4 | — |
| 62 | 4 | 4 | — |
| 63 | 0 | 0 | — |
| 64 | 4 | 3 | — |
| 67 | 4 | 4** | — |
| 70 | 3 | 0 | — |
| 72 | 4 | — | 2 |
| 73 | 4 | — | 2 |
| 76 | 4 | — | 3 |
| 78 | 4 | — | 2 |
| 80 | 1 | — | 0 |
| 81 | 4 | — | 2 |
| 82 | 2 | — | 0 |
| 83 | 4 | — | 2 |
| 84 | 4 | — | 1 |

**Protectant test at 100 ppm.

We claim:

1. A compound of the formula

wherein $R^1$ is (a) a phenyl group optionally substituted by one or more halogen atoms, cyano groups, $C_1$ to $C_6$ alkoxy groups, methylene- or ethylene-dioxy groups, $C_1$ to $C_6$ alkyl groups, or $C_1$ to $C_6$ haloalkyl groups or (b) a heteroaromatic group selected from the group consisting of furyl, thiophenyl, and pyridyl optionally substituted by one or more $C_1$ to $C_6$ alkyl groups, $C_1$ to $C_6$ haloalkyl groups or halogen atoms; X is a halogen or hydroxy; and Y is $CONH_2$ or $COOCH_3$, $R^1$ being other than unsubstituted phenyl when Y is $COOCH_3$ and X is OH.

2. A compound according to claim 1 wherein X is bromine.

* * * * *